United States Patent
Lubock et al.

(10) Patent No.: US 7,407,476 B2
(45) Date of Patent: *Aug. 5, 2008

(54) TISSUE IRRADIATION WITH SHIELDING

(75) Inventors: Paul Lubock, Laguna Niguel, CA (US); Michael L. Jones, San Clemente, CA (US)

(73) Assignee: SenoRx, Inc., Aliso Viejo, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/593,952

(22) Filed: Nov. 6, 2006

(65) Prior Publication Data

US 2007/0191668 A1    Aug. 16, 2007

Related U.S. Application Data

(63) Continuation of application No. 11/283,236, filed on Nov. 18, 2005.

(60) Provisional application No. 60/819,919, filed on Jul. 11, 2006, provisional application No. 60/819,920, filed on Jul. 11, 2006, provisional application No. 60/774,266, filed on Feb. 16, 2006.

(51) Int. Cl.
*A61N 5/00* (2006.01)

(52) U.S. Cl. .......................................... 600/3

(58) Field of Classification Search ........ 600/1–9, 600/30, 407, 424, 427; 601/1, 15, 111, 112, 601/118, 119; 604/19–21, 27–28, 48, 73, 604/93.01, 95.03, 96.01, 101.01–101.05, 604/102.01–102.03, 103.05–103.07, 103.1, 604/104, 158–159, 164.01, 164.08, 171, 604/263–264, 500, 506–511, 514–517; 606/1, 606/32–34, 41; 607/1–2, 100, 101, 122, 607/154–156
See application file for complete search history.

(56) References Cited

U.S. PATENT DOCUMENTS 3,872,856 A    3/1975    Clayton (Continued)

FOREIGN PATENT DOCUMENTS

| EP | 0 642 766 | 3/1995 |
|---|---|---|
| EP | 0 719 571 | 7/1996 |
| EP | 0 867 200 | 9/1998 |

(Continued)

OTHER PUBLICATIONS

International Search Report for PCT/US2006/043891 mailed May 11, 2007.
"Variable shield for radiation-therapy source wire and centering catheter", Research disclosure, Mason Publications, Hampshire, GB, vol. 438, No. 48, Oct. 2000, XP007126916.
International Search Report for PCT/US2006/043891 mailed Sep. 25, 2007.
Written Opinion of the International Searching Authority for PCT/US2006/043891 mailed Sep. 25, 2007.

*Primary Examiner*—John P Lacyk
(74) *Attorney, Agent, or Firm*—Edward J. Lynch (57) ABSTRACT

Devices and methods are disclosed for treatment to tissue surrounding a body cavity or other intracorporeal site, such as after removal of tissue, e.g. cancer. Such a device includes a treatment location on a distal portion of the device with one or more radiation shielding components that partially encircle a radiation source at the treatment location to control emitted radiation from the radiation source. The device minimizes radiation damage to healthy tissue surrounding the body cavity or other site while irradiating tissue not shielded by the radiation shielding components. A device embodying features of the invention can include a sealing member at a location on a shaft of the device proximal to a treatment location to seal the passageway leading to the body cavity.

37 Claims, 11 Drawing Sheets

U.S. PATENT DOCUMENTS

| | | | |
|---|---|---|---|
| 4,690,677 | A | 9/1987 | Erb |
| 5,621,780 | A | 4/1997 | Smith et al. |
| 5,935,098 | A | 8/1999 | Blaisdell et al. |
| 6,036,631 | A | 3/2000 | McGrath et al. |
| 6,390,967 | B1 | 5/2002 | Forman et al. |
| 6,398,708 | B1 | 6/2002 | Hastings et al. |
| 6,413,203 | B1 * | 7/2002 | Sahatjian ............ 600/3 |
| 6,413,204 | B1 | 7/2002 | Winkler et al. |
| 6,416,492 | B1 | 7/2002 | Nielson |
| 6,482,142 | B1 | 11/2002 | Winkler et al. |
| 6,540,655 | B1 * | 4/2003 | Chin et al. ............ 600/3 |
| 6,706,014 | B2 | 3/2004 | Banik et al. |
| 6,752,752 | B2 | 6/2004 | Geitz |
| 6,913,600 | B2 | 7/2005 | Valley et al. |
| 6,923,754 | B2 | 8/2005 | Lubock |
| 2001/0016725 | A1 * | 8/2001 | Valley et al. ............ 604/509 |
| 2004/0054366 | A1 | 3/2004 | Davison et al. |
| 2005/0080313 | A1 * | 4/2005 | Stewart et al. ............ 600/3 |
| 2005/0124843 | A1 | 6/2005 | Singh |
| 2006/0100475 | A1 | 5/2006 | White et al. |

FOREIGN PATENT DOCUMENTS

| | | |
|---|---|---|
| EP | 1 402 922 | 3/2004 |
| EP | 1 618 924 | 1/2006 |
| WO | WO 95/20241 | 7/1995 |
| WO | WO 97/45053 | 12/1997 |
| WO | WO 01/43826 | 6/2001 |
| WO | WO 01/58346 | 8/2001 |
| WO | WO 2004/043531 | 5/2004 |
| WO | WO 2007/027831 | 3/2007 |

* cited by examiner

TISSUE IRRADIATION WITH SHIELDING

RELATED APPLICATIONS

This application is a continuation of and claims priority from application Ser. No. 11/283,236 filed on Nov. 18, 2005, which was filed base on the priority of provisional application Ser. No. 60/819,919, filed on Jul. 11, 2006, both of which are incorporated herein by reference in their entirety. This application also claims priority to provisional applications Ser. No. 60/774,266, filed Feb. 16, 2006 and Ser. No. 60/819,920, filed Jul. 11, 2006.

FIELD OF THE INVENTION

This invention relates generally to the fields of medical treatment devices and methods. In particular, the invention relates to devices and methods for treating tissue surrounding a body cavity, such as a site from which cancerous, precancerous, or other tissue has been removed.

BACKGROUND OF THE INVENTION

In diagnosing and treating certain medical conditions, it is often desirable to perform a biopsy, in which a specimen or sample of tissue is removed for pathological examination, tests and analysis. A biopsy typically results in a biopsy cavity occupying the space formerly occupied by the tissue that was removed. As is known, obtaining a tissue sample by biopsy and the subsequent examination are typically employed in the diagnosis of cancers and other malignant tumors, or to confirm that a suspected lesion or tumor is not malignant. Treatment of cancers identified by biopsy may include subsequent removal of tissue surrounding the biopsy site, leaving an enlarged cavity in the patient's body. Cancerous tissue is often treated by application of radiation, by chemotherapy, or by thermal treatment (e.g., local heating, cryogenic therapy, and other treatments to heat, cool, or freeze tissue).

Cancer treatment may be directed to a natural cavity, or to a cavity in a patient's body from which tissue has been removed, typically following removal of cancerous tissue during a biopsy or surgical procedure. For example, U.S. Pat. No. 6,923,754 to Lubock and U.S. patent application Ser. No. 10/849,410 to Lubock, the disclosures of which are all hereby incorporated by reference in their entireties, describe devices for implantation into a cavity resulting from the removal of cancerous tissue which can be used to deliver cancer treatments to surrounding tissue. One form of radiation treatment used to treat cancer near a body cavity remaining following removal of tissue is "brachytherapy" in which a source of radiation is placed near to the site to be treated.

Lubock above describes implantable devices for treating tissue surrounding a cavity left by surgical removal of cancerous or other tissue that includes an inflatable balloon constructed for placement in the cavity. Such devices may be used to apply one or more of radiation therapy, chemotherapy, and thermal therapy to the tissue surrounding the cavity from which the tissue was removed. The delivery lumen of the device may receive a solid or a liquid radiation source. Radiation treatment is applied to tissue adjacent the balloon of the device by placing radioactive material such as radioactive "seeds" in a delivery lumen. Such treatments may be repeated if desired.

For example, a "MammoSite® Radiation Therapy System" (MammoSite® RTS, Proxima Therapeutics, Inc., Alpharetta, Ga. 30005 USA) includes a balloon catheter with a radiation source that can be placed within a tumor resection cavity in a breast after a lumpectomy. It can deliver a prescribed dose of radiation from inside the tumor resection cavity to the tissue surrounding the original tumor. The radiation source is typically a solid radiation source; however, a liquid radiation source may also be used with a balloon catheter placed within a body cavity (e.g., lotrex®, Proxima Therapeutics, Inc.). A radiation source such as a miniature or microminiature x-ray tube may also be used (e.g. U.S. Pat. No. 6,319,188). The x-ray tubes are small, flexible and are believed to be maneuverable enough to reach the desired treatment location within a patient's body. The radiation source is to be removed following each treatment session, or remains in place as long as the balloon remains within the body cavity. Inflatable treatment delivery devices and systems, such as the MammoSite® RTS and similar devices and systems (e.g., GliaSite® RTS (Proxima Therapeutics, Inc.)), are useful to treat cancer in tissue adjacent a body cavity.

However, radiation, chemotherapy, thermal treatment, and other cancer treatments often have deleterious effects on healthy tissue in addition to the desired effects on cancerous tissue. In such treatments, care must be taken to direct the maximum treatment effects to diseased tissue while minimizing its delivery or effects on healthy tissue. For example, radiation treatment may be most effective when only the portion of tissue requiring treatment receives the radiation and where surrounding healthy tissue is unaffected. Tissue cavities typically are not uniform or regular in their sizes and shapes, so that differences in dosages applied to different regions of surrounding tissue, including "hot spots" and regions of relatively low dosage, often result from radiation treatment.

A treatment delivery device for treating tissue adjacent a body cavity has been disclosed in U.S. Pat. No. 6,923,754. This device applies a partial-vacuum or suction to bring tissue towards a radiation source and allows for uniform application of radiation to tissue surrounding a body cavity. An advantage of the present invention is that it allows for the protection of healthy tissue within that body cavity and provides a seal in the passageway leading to the body cavity while treating the desired tissue.

SUMMARY OF THE INVENTION

This invention is generally directed to treating a patient's body cavity or other intracorporeal site, such as by irradiation, and devices and methods for such treatments. The invention is particularly suitable for treating tissue adjacent a patient's body cavity formed by removal of tissue for a biopsy.

More specifically, a device embodying features of the invention includes a treatment location at a distal portion thereof which is configured to receive or which includes a source for a treatment agent, such as a radiation source. The distal portion of the device has one or more radiation shielding components that partially surround the treatment in order to absorb part of the radiation emitted from the radiation source to thereby protect tissue defining the cavity which is shielded by the shielding component and to allow irradiation treatment of tissue defining the cavity which is not shielded by the shielding component.

The radiation shielding component is designed to reduce or minimize damaging irradiation of healthy tissue which surrounds the body cavity or other site while treating nearby areas having diseased tissue with radiation emitted from the radiation source. The radiation shielding components include one or more radiation shields disposed about a delivery shaft containing the radiation source. The radiation shielding component may also include radiation shields proximal and/or distal to the treatment location to control axial and near axial radiation emissions of the radiation source. The location of the pair of radiation shields may be configured to be adjustable to accommodate anatomical structural variations or to adjust treatment parameters. The radiation shield which partially encircles the treatment location preferably has or defines at least in part a window to control the dispersal of radiation from a radiation source. The window defined at least in part by the centrally located radiation shield has a length between about 2 millimeters and 5 centimeters. The shielded area of the centrally located radiation shield is arcuate with an angular range from about 20° to about 240°. While the centrally located radiation shield may be utilized by itself, preferably, it is configured to be deployed between the proximal and distal shields such as discussed above.

The shielding component may be one or more separate shielding elements formed at least in part of radiation absorbing materials or, alternatively, the shielding component may be a radiation absorbing material coat onto or incorporated within the device. The radiation absorbing material can extend over various locations on the cavity filling member depending upon the needs of the particular procedure. Preferably, coatings of radiation absorbing material should be located on a cavity filling member surrounding the treatment location so as to be between the radiation source within the cavity filing member and tissue surrounding the treatment location which might be damaged by the radiation, e.g. the patient's skin. For example, if the device is inserted into the patient's breast from a location where the cavity filling member is closer to tissue to be protected that the insertion site, the radiation absorbing material can extend longitudinally along the cavity filling member. If the catheter device is inserted into the patient's breast from a location where the tissue to be protected is at the insertion site, radiation absorbing material may cover an end of the cavity filling member. Other configurations may be provided depending upon the needs of the procedure.

A device embodying features of the invention preferably has an elongated shaft with an inner lumen extending from a proximal shaft portion to the treatment location in the distal shaft portion configured to guide a treatment agent such as a radiation source to the treatment location. Additionally, the device has a cavity filling member on the distal shaft portion which surrounds at least in part the treatment location and which is configured to at least partially fill the cavity or intracorporeal site to be treated. The device may also be provided with one or more vacuum lumens within the elongated shaft which are configured to be in communication with a vacuum source at a proximal end thereof and in communication with one or more exterior vacuum ports in the distal shaft portion. By applying a vacuum to the body cavity or other intracorporeal site, tissue surrounding the cavity filling member can be made to conform to the exterior of the cavity filling member so as to provide a more uniform irradiation of tissue surrounding the cavity or intracorporeal site.

The cavity filling member embodying features of the invention preferably is enlarged or enlargeable at the treatment location to at least in part fill the body cavity. Preferably the cavity filling member is inflatable such as a balloon. An inner lumen is provided in the elongated shaft which is in fluid communication with the inflatable cavity filling member. The vacuum ports of a preferred device has vacuum ports proximal and or distal to the cavity filling member such as described in U.S. Pat. No. 6,923,754 and application Ser. No. 10/849,410 filed on May 19, 2004, both of which are assigned to the present assignee. Application of a vacuum within the inner lumen may also be employed to aspirate fluid in the cavity or other site through the one or more vacuum ports.

The elongated shaft of the device may have one or more additional inner lumens which are configured to lead one or more radiation shielding members to the treatment location.

A method for treating a body cavity or other intracorporeal site of a patient include delivering a source for a treatment agent such as a radiation source to a body cavity or other site to treat the desired tissue defining or otherwise surrounding in part the cavity or site while minimizing damaging irradiation of healthy tissue defining or otherwise surrounding in part the cavity or site. More specifically, a method for treating a body cavity includes providing a device having a treatment location in a distal portion of the device with a radiation source configured to be deposited in the treatment location and a radiation shielding component partially encircling the treatment location and configured to control in part the emission of radiation emitted from the treatment location. The device is advanced within the patient until the distal portion of the device having the treatment location is disposed within the body cavity or other site and the radiation source is positioned within the treatment location. The radiation shielding component is positioned to shield portions of the body cavity or other site from radiation emitted from the radiation source.

Placing patterns or radiation absorbing materials on the surface or within the cavity filling member such as the wall of the cavity filling member (e.g. balloon) would aid in shielding the skin or in other cases sensitive organs (e.g., heart, lung, etc.) from unnecessary radiation. Examples of radiation absorbing materials include—mylar with aluminum, balloon coatings with gold, lead, titanium barium and barium sulfate or silver ions incorporated within the balloon wall.

The surface (inside or outside) of the balloon or within the balloon wall may be provided with indicator marks for location or orientation detection during the procedures. For example, dots or lines to help place balloon in appropriate position under CT, x-ray, fluoroscopy. The indicator marks may be radiopaque. Alternatively, or additionally, ultrasound indicators or MRI and direct visual indicators could be incorporated. The indicator marks may extend along the catheter shaft to help with placement of the catheter device during the treatment procedure.

In other embodiments having features of the invention, the radiation shield may be secured to a control rod or band within the catheter device so that the location of the shield may be adjusted. Alternatively, the radiation shield may be secured within or onto the catheter device.

A device embodying features of another aspect of the invention includes an elongate shaft with a sealing member located on the elongate shaft proximal to the treatment location to seal the intracorporeal passageway through which the device is advanced. The sealing member is expanded or expandable and configured to minimize the loss of vacuum within the body cavity when a vacuum is developed therein. Preferably the sealing member is also configured to seal the passageway when aspirating fluid from the body cavity or delivering fluid, e.g. treatment fluid, to the body cavity.

A patient's skin is susceptible to damage from radiation delivered by isotopes (e.g. seeds) or x-ray catheters in a lumen of a radiation balloon catheter if the radiation source is to close to the skin. Radiation treatments using a radiation balloon catheter are usually not performed on patients where the body cavity (e.g. from a lumpectomy) is less than 5 mm, sometimes less than 7 mm from the patient's skin. The application of a vacuum to the body cavity may help to conform the cavity tissue to the cavity filling member and increase cavity to skin surface distances. Over extending the cavity by over inflation of the balloon which can thin and stretch the skin. In some instances it would still be too thin to treat. The number of potential patients which are suitable candidates for treatments with radiation balloons is significantly reduce due to the potential for skin tissue damage.

Enhanced control over the emission of radiation from a radiation source and an improved seal in the passageway leading to the body cavity are provided by the present invention which increases considerably the number of potential patients which are suitable candidates for radiation treatments. These and other advantages of the present invention are described in more detail in the following written description and the accompanying exemplary drawings.

DETAILED DESCRIPTION OF THE INVENTION

The present invention provides devices and methods for treatment of a patient's body cavity or other intracorporeal site. For example, devices and methods having features of the invention are used to deliver treatment into a biopsy site or into a cavity or site left after removal of cancerous tissue from the patient's body.

As shown in FIGS. 1A-1D a tissue treating device 10 embodying features of the invention includes an elongated shaft 12 with a treatment location 14 in a distal portion 16 of the elongate shaft 12. The treatment location 14 includes a source for a treatment agent such as a radiation source 18 which has a push rod 20 for advancing the source within the device. The elongate shaft 12 has a delivery lumen 22 which leads to treatment location 14 for advancement of the radiation source 18 to the treatment location. The elongated shaft 12 also includes a delivery port 24 in fluid communication with the delivery lumen 22 through which the radiation source 18 is advanced. The device 10 has one or more radiation shielding components 26 disposed about the radiation source 18 deployed within the treatment location to control in part the radiation emitted from the radiation source. The radiation shielding component 26 is designed to reduce or minimize damaging irradiation of healthy tissue surrounding a body cavity while treating nearby areas having diseased tissue with radiation emitted from the radiation source 18.

Figure 2A:
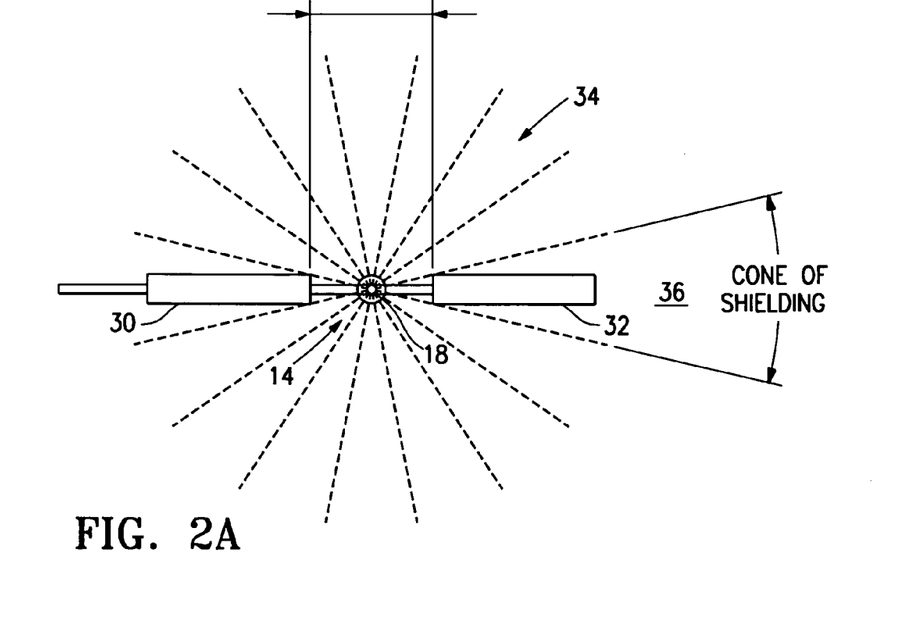
FIGS. 2A and 2B are diagramatic views of a radiation shielding component which includes a proximal radiation shield and a distal radiation shield.
Figure 2B:
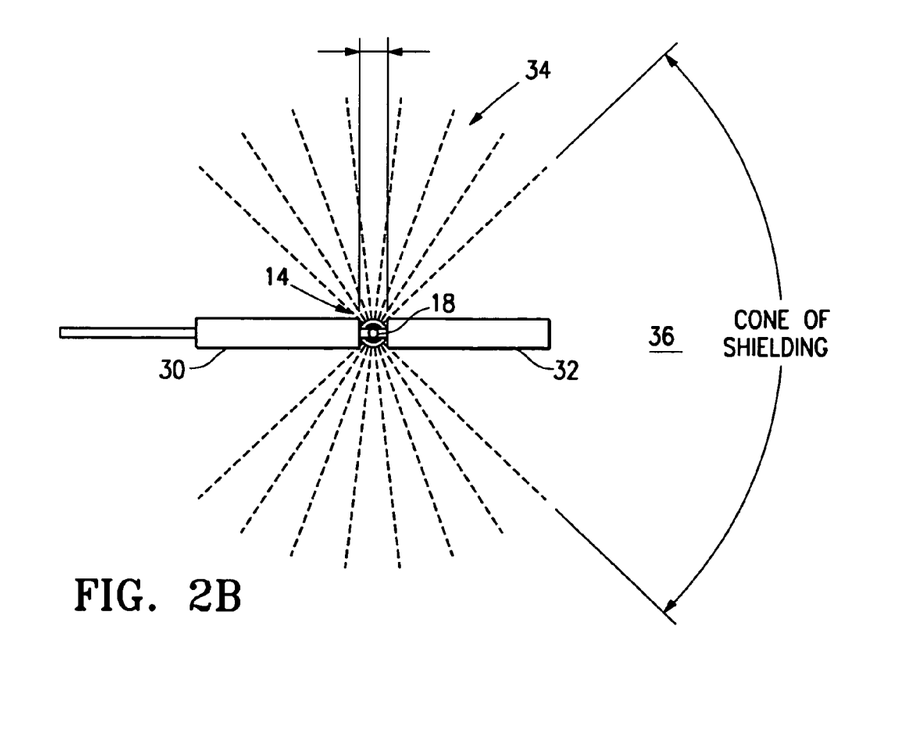

The radiation shielding component 26 includes at least one radiation shield 28 which is configured to be deployed proximal to, distal to, or within the treatment location 14. Preferably, the radiation shielding component 26 has a pair of radiation shields including a proximal radiation shield 30 and a distal radiation shield 32 (FIGS. 2A-2B). The proximal shield 30 is deployed proximal to the treatment location 14 and the distal shield 32 is deployed distal to the treatment location 14. The shields allow for control, at least in part, of the axial and near axial emissions from the proximal and distal end portions of the elongate shaft 12. When the proximal end of distal radiation shield 32 is adjacent the radiation source 18 and the distal end of the proximal radiation shield 30 is adjacent the radiation source 18 the radiation dispersal pattern 34 would be a small cone emanating from the radiation source 18. As the proximal end of the distal radiation shield 32 and the distal end of the proximal radiation shield 30 move further away from the radiation source 18 the radiation dispersal pattern 34 increases to a near spherical shape having an axial cone of shielding 36 expanding from the radiation source 18 along the longitudinal axis in both directions. The pair of radiation shields 30 and 32 are preferably configured to be adjustable to accommodate anatomical structural variations or to adjust treatment parameters.

The radiation shielding component 26 includes one or more radiation shields 28. The radiation shields 28 are formed of a suitably radiopaque metal or polymer containing at least in part a radiation absorbing material and are preferably tubular. The shields are preferably slidably disposed about the delivery lumen 22 of the device 10. Suitable radiation absorbing materials include tantalum, bismuth subcarbonate, barium sulfate, platinum, gold and tungsten.

The radiation source 18 of the device 10 can include a radiation source which is solid or liquid. Suitable liquid radiation sources include, for example, a liquid containing a radioactive iodine isotope (e.g., $I^{125}$ or $I^{131}$), a slurry of a solid isotope, for example, $^{198}$Au or $^{169}$Yb, or a gel containing a radioactive isotope. Liquid radiation sources are commercially available (e.g., Iotrex®, Proxima Therapeutics, Inc., Alpharetta, Ga.). The radiation source 18 preferably includes brachytherapy seeds or other solid radiation sources used in radiation therapy, for example, a radioactive microsphere available from 3M Company of St. Paul, Minn. The radiation source 18 is either preloaded into the device 10 at the time of manufacture or is loaded into the device 10 after placement into a body cavity of a patient. Solid radionuclides suitable for use with a device 10 embodying features of the present invention are currently generally available as brachytherapy radiation sources (e.g., I-Plant.™., Med-Tec, Orange City, Iowa.). Radiation may also be delivered by a device such as the x-ray tube of U.S. Pat. No. 6,319,188. The x-ray tubes are small, flexible and are believed to be capable of being maneuverable enough to reach the desired location within a patient's body.

Figure 1A:
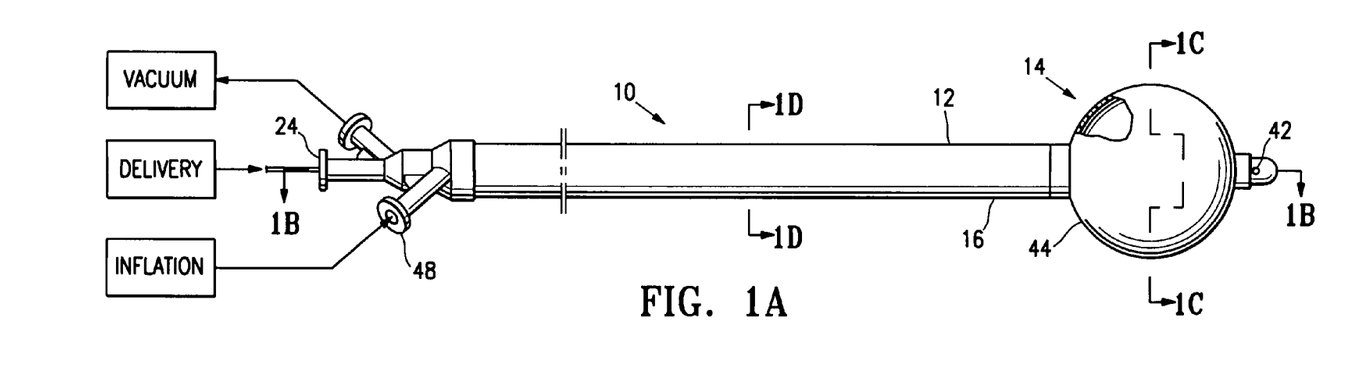
FIG. 1A is a schematic view of a device embodying features of the invention including a cavity filling member.
Figure 1B:
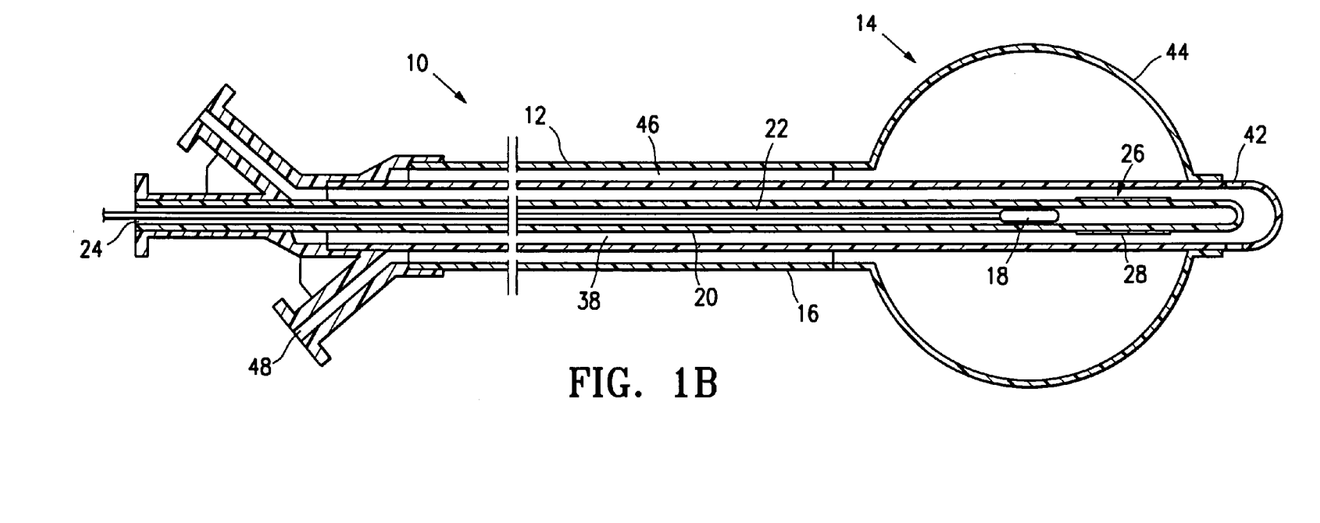
FIG. 1B is a longitudinal cross sectional view of the device along lines 1B-1B in FIG. 1A.
Figure 1C:
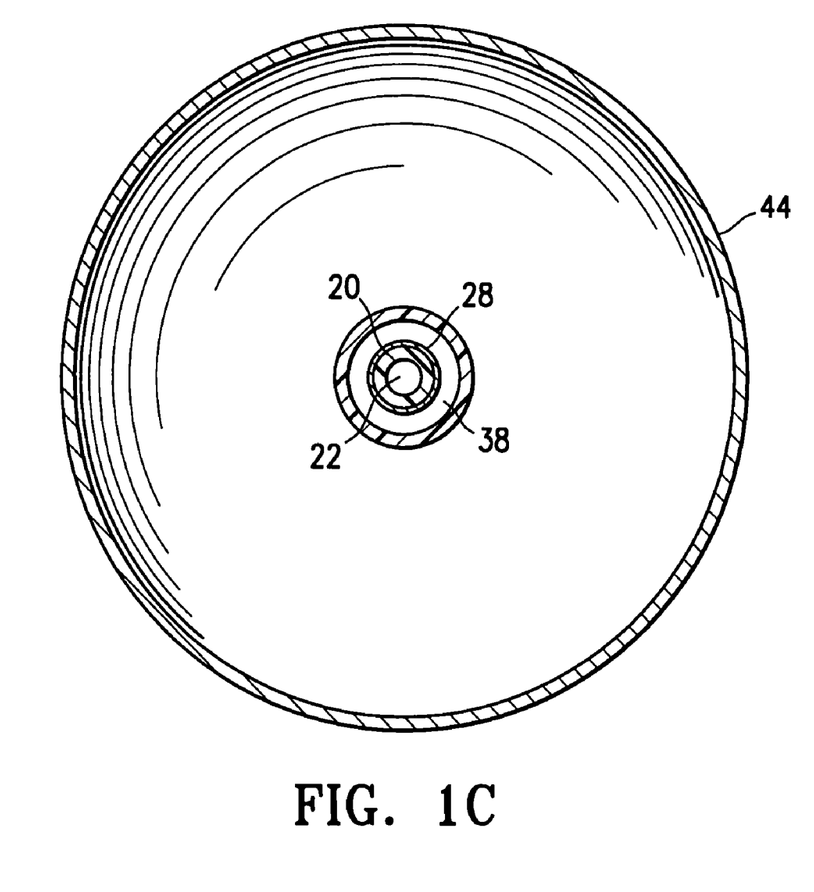
FIG. 1C is a transverse cross sectional view of the device taken along lines 1C-1C in FIG. 1A.
Figure 1D:
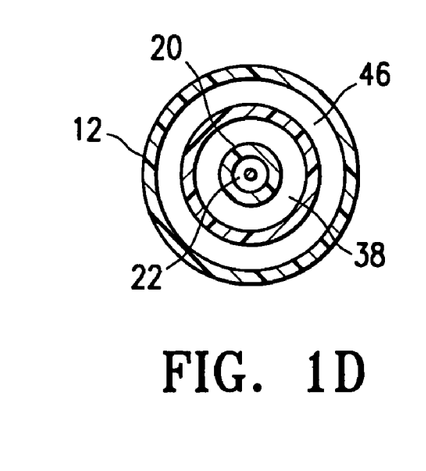
FIG. 1D is a transverse cross sectional view of the device taken along lines 1D-1D.

One embodiment of the device 10 also includes a vacuum lumen 38 which is configured to be in fluid communication with a vacuum source (not shown) and one or more vacuum ports 42 in the exterior of the distal portion of the elongated shaft 12. The vacuum ports 42 are in fluid communication with the vacuum lumen 38 to provide a vacuum within a body cavity or other intracorporeal site.

In one embodiment the device 10 includes a cavity filling member 44 on the distal portion 16 of the shaft 12 which at least in part fills the body cavity or other site. The cavity filling member 44 can be inflatable or expandable and configured to contact tissue surfaces defining the body cavity. The cavity filling member 44 is in fluid communication with a first inflation lumen 46 which has a first inflation port 48. The vacuum ports 42 for the vacuum lumen 38 preferably are located proximal and or distal to the cavity filling member 44 which at least partially fills the body cavity.

Figure 3A:
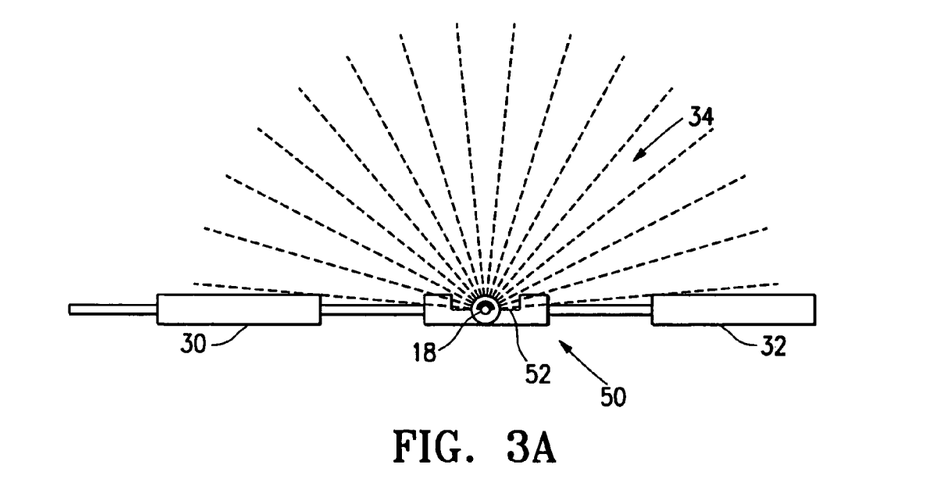
FIG. 3A is a diagramatic view of a central radiation shield which is configured to partially encircle the treatment location so as to control the emissions from a radiation source at the treatment location.
Figure 3B:
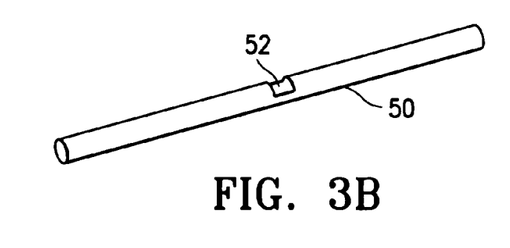
FIG. 3B is a perspective view of a central radiation shield including a window.
Figure 3C:
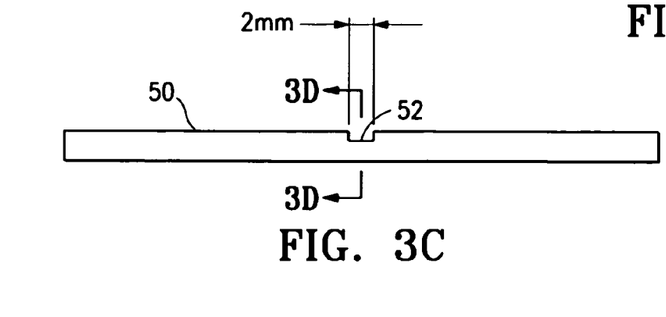
FIG. 3C is an elevational view of the central radiation shield shown in FIG. 3B.
Figure 3D:
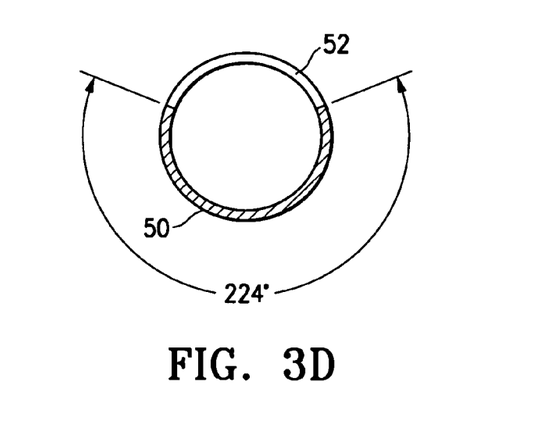
FIG. 3D is a transverse cross sectional view of the central radiation shield taken along lines 3D-3D in FIG. 3C.
Figure 3E:
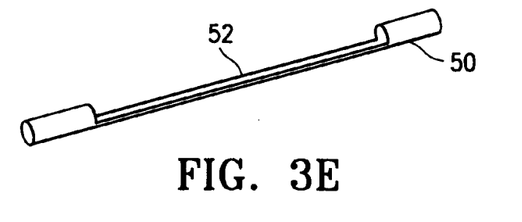
FIG. 3E is a perspective view of a central radiation shield including a window similar to but longer than the window shown in FIG. 3B.
Figure 3F:
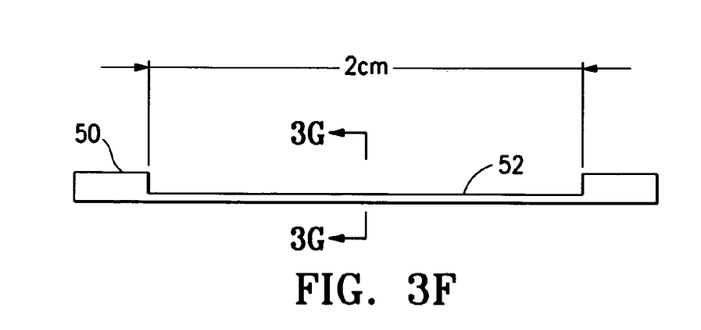
FIG. 3F is an elevational view of the central radiation shield shown in FIG. 3E.
Figure 3G:
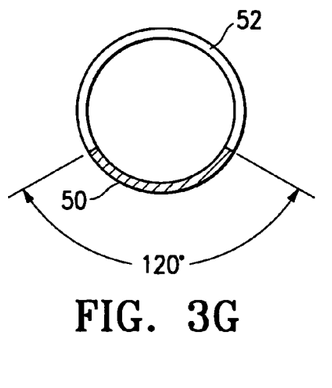
FIG. 3G is a transverse cross sectional view of the central radiation shield taken along lines 3G-3G in FIG. 3F.

A central radiation shield 50, shown in FIG. 3A, can be deployed between the proximal 30 and distal 32 radiation shields. The central radiation shield 50 preferably defines at least in part a window 52 to allow for dispersal of radiation from a radiation source 18. Preferably the central radiation shield 50 defines a window 52 which may have a variable length as shown in FIGS. 3B-G. Preferably the length of the window 52 is between about 2 millimeters to 5 centimeters and the central radiation shield is tubular in shape. Preferably the shielding area is arcuate with an angular range from about 20° to about 240°. Alternatively the central radiation shield 50 comprises a pair of separately rotatable members to allow for adjusting the window dimensions. The central radiation shield 50 is rotated or advanced to position the window 52 near the target tissue.

Figure 4A:
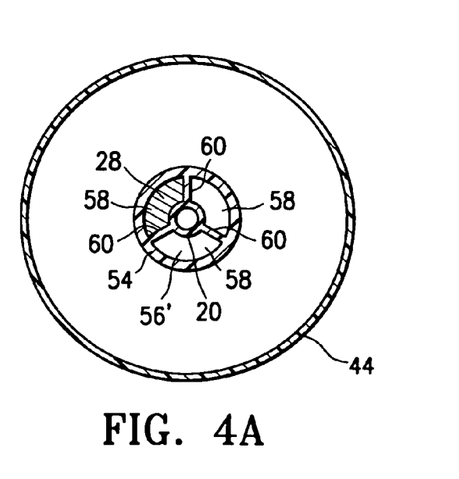
FIGS. 4A and 4B are transverse cross sectional views of an elongated shaft of a device embodying features of the invention which includes three chambers, some of which contain radiation shields.
Figure 4B:
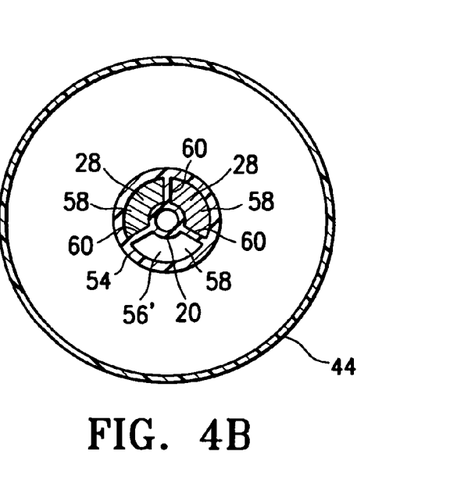

Another embodiment of the invention shown in FIGS. 4A and 4B includes a partitioned shaft 54 disposed about the delivery shaft 20. The partitioned shaft 54 has a lumen 56 which is divided into at least two chambers 58 by spacing elements 60. Radiation shields 28 are configured to be inserted into one or more chambers 58 through the proximal end of the elongate shaft 12 to surround at least a portion of the treatment location 14. The radiation shields 28 reduce or minimize irradiation of healthy portions of the body cavity while treating nearby areas with the radiation source 18.

In one possible embodiment the radiation shield 28 has varying densities acting as a filter to allow for some controlled amount of radiation to pass through yielding a non-symmetric radiation dosing. In another embodiment the radiation shields 28 are constructed of sintered metal to block radiation and still allow for a fluid pathway for suction or vacuum of the body cavity.

Figures 5A, 5B, 6:
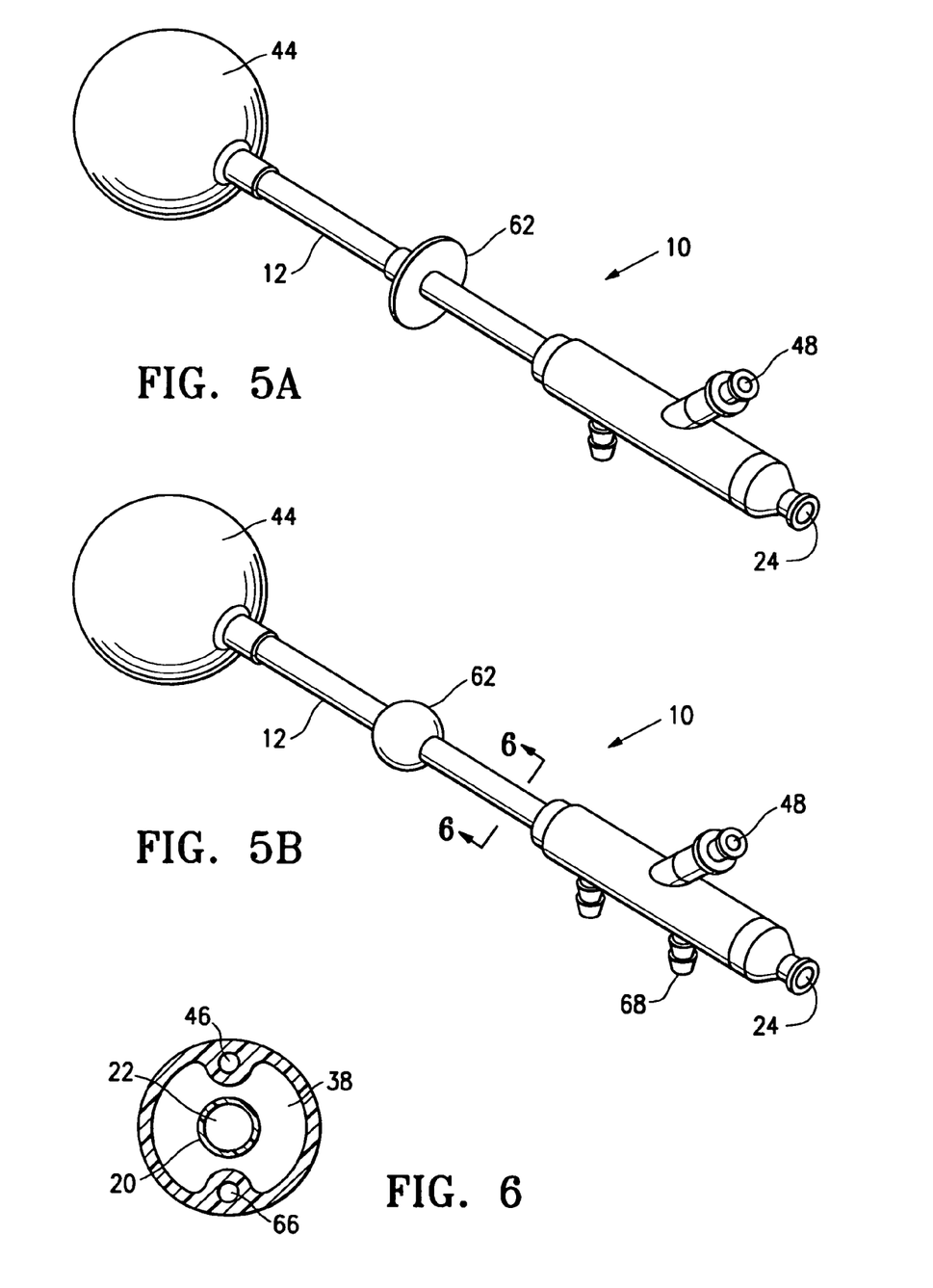
FIG. 5A is perspective view of a device embodying features of the invention including a sealing member which is formed of an adhesive material.
FIG. 5B is a perspective view of a device embodying features of the invention including an inflatable sealing member.
FIG. 6 is a cross sectional view of the device shown in FIG. 5B taken along line 6-6.

In another embodiment of the invention depicted in FIGS. 5A, 5B and 6 the device includes an elongate shaft 12 with a sealing member 62 located on the elongate shaft 12 to seal the passageway 64 through which the device 10 is advanced. The sealing member can be inflated via a second inflation lumen 66 (FIGS. 5B and 6A) which is in fluid communication with a second inflation port 68 on the proximal end of the elongate shaft 12. The sealing member 62 allows for closer contact with the walls of the passageway 64. Preferably, the device 10 also includes a cavity filling member 44 which at least in part fills the body cavity and which is inflatable or expandable. The sealing member 62 is located on the elongate shaft 12 proximal to the distal end of the elongate shaft.

Alternatively, as shown in FIG. 5A, the device 10 can include a sealing member 62 formed of a flange or cuff having an adhesive distal face and located toward the proximal end of the elongate shaft 12. The sealing member 62 preferably is configured to form a seal in the passageway 64 leading to the body cavity by adhering to a patient's skin.

The device 10 preferably includes a vacuum lumen 38 configured to be in fluid communication with a proximal vacuum source and one or more vacuum ports 42 preferably proximal and or distal to the cavity filling member 44. Application of a vacuum within the vacuum lumen 38 aspirates fluid in the cavity through one or more vacuum ports 42 and pulls tissue surrounding the cavity onto the exterior of the cavity filling member 44 deployed within the cavity. As shown in FIG. 5B the sealing member 62 preferably is expanded or expandable, such as a balloon, and configured to minimize the loss of vacuum within the body cavity when a vacuum is developed.

A device 10 having features of the invention can include contoured pads for use on the elongate shaft 12 of the device 10. The contoured pads are provided on the proximal portion of the elongated shaft 12 of the device 10 and are configured to cover a portion of the shaft. The contoured pads preferably are comprised of material having soft tapered edges to minimize irritation to the skin caused by movement or dressing and undressing. The pads are taped externally to the patient or alternatively are attached to the patient with a double sided tape or adhesive material.

A device 10 having features of the invention can be provided, at least in part, with a lubricious coating, such as a hydrophilic material. The lubricious coating preferably is applied to the elongate shaft 12 or to the cavity filling member 44, if one is present, to reduce sticking and friction during insertion of a device 10. Hydrophilic coatings such as those provided by AST, Surmodics, TUA Systems, Hydromer, or STS Biopolymers are suitable.

A device 10 having features of the invention may also include an antimicrobial coating that covers all or a portion of the device 10 to minimize the risk of introducing of an infection during extended treatments. The antimicrobial coating preferably is comprised of silver ions impregnated into a hydrophilic carrier. Alternatively the silver ions are implanted onto the surface of the device 10 by ion beam deposition. The antimicrobial coating preferably is be comprised of an antiseptic or disinfectant such as chlorhexadiene, benzyl chloride or other suitable biocompatible antimicrobial materials impregnated into hydrophilic coatings. Antimicrobial coatings such as those provided by Spire, AST, Algon, Surfacine, Ion Fusion, or Bacterin International would be suitable. Alternatively a cuff member covered with the antimicrobial coating is provided on the elongated shaft of the delivery device 10 at the point where the device 10 enters the skin.

Figure 7A:
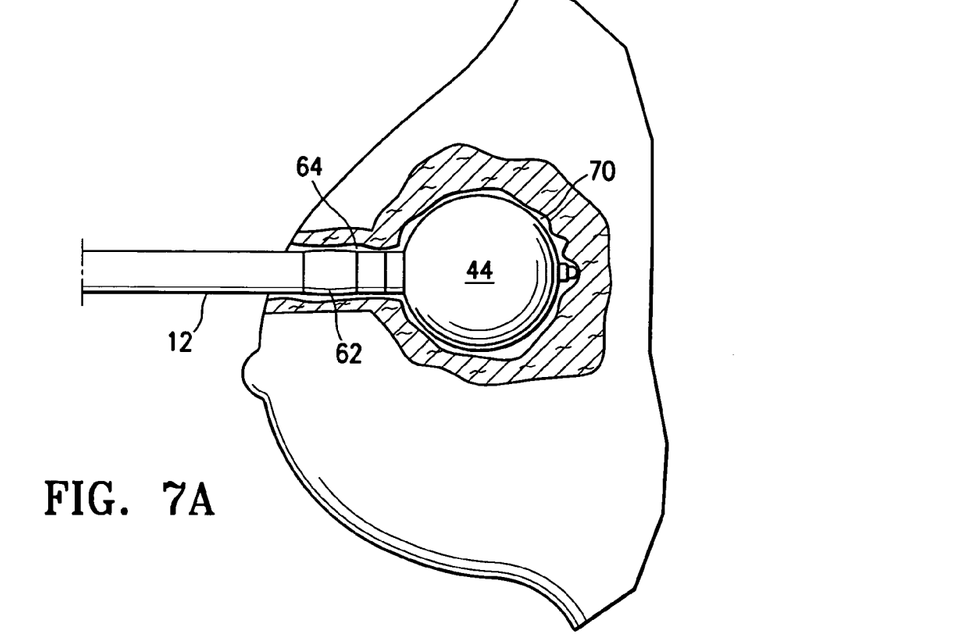
FIGS. 7A and 7B show the steps of a method for treating a body cavity utilizing the device shown in FIG. 5B.
Figure 7B:
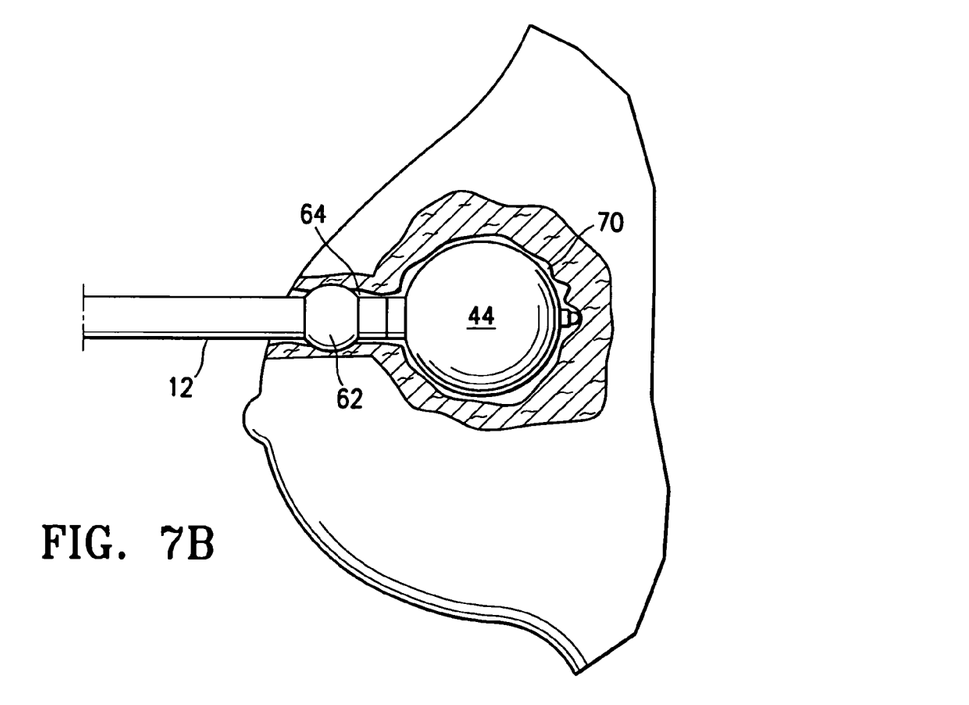

A method for treating a body cavity 70 of a patient is shown in FIGS. 7A and 7B. The method includes delivering a radiation source 18 to a body cavity 70 to treat the desired tissue adjacent a device 10 embodying features of the invention while minimizing damaging irradiation of healthy tissue. For example, the method includes inserting a device 10 embodying features of the invention into the body cavity 70, positioning a radiation shielding component 26 to shield healthy tissue in the body cavity 70 and positioning a source for a treatment agent, such as radiation source 18 within the treatment location 14 in a distal portion 16 of the shaft 12.

A method for treating tissue adjacent a body cavity 70 may also include sealing a passageway 64 leading to a body cavity 70. For example, the method includes inserting a device 10 embodying features of the invention into the body cavity 70 and sealing the passageway 64 leading to the body cavity 70 (FIG. 7A) and then at least in part contacting the passageway 64 with a sealing member 62 on the elongate shaft 12 (FIG. 7B).

Figure 8:
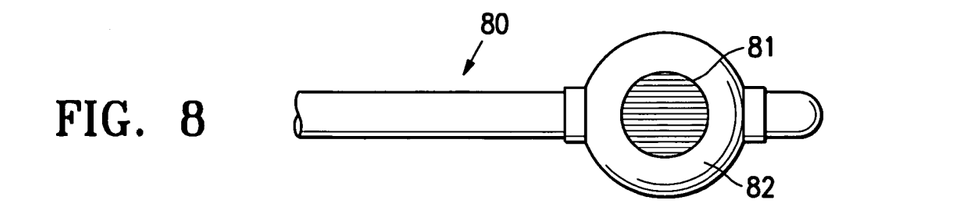
FIG. 8 is a partial elevational view of a distal portion of a radiation balloon catheter device having a circular radiation shield region on the balloon.
Figure 9A:
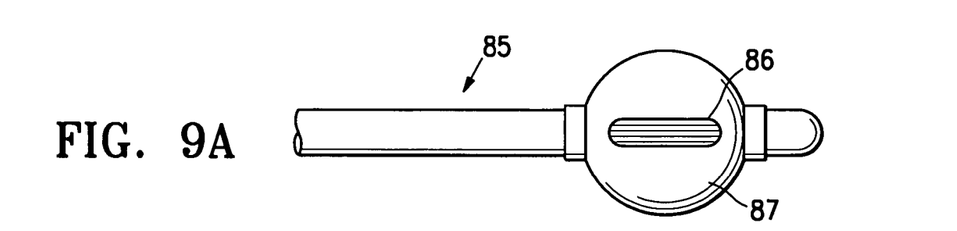
FIGS. 9A and 9B are partial elevational views of distal portions of radiation balloon catheter devices having elongated radiation shield regions (oval and lenticular shaped) on the balloon.
Figure 9B:
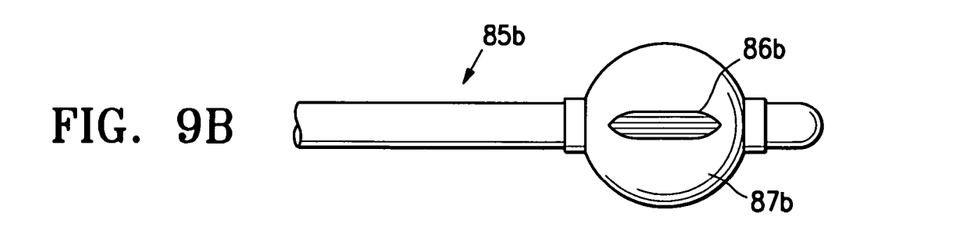

FIG. 8 illustrates a radiation balloon catheter device 80 having a circular radiation absorbing region 81 on the balloon 82 of the catheter device. FIG. 9A illustrates a radiation balloon catheter device 85 having an elongated radiation absorbing region 86 on balloon 87. FIG. 9B illustrates an alternative structure to that shown in FIG. 9A where the elongated radiation region 86b tapers at the ends thereof.

Figure 10A:
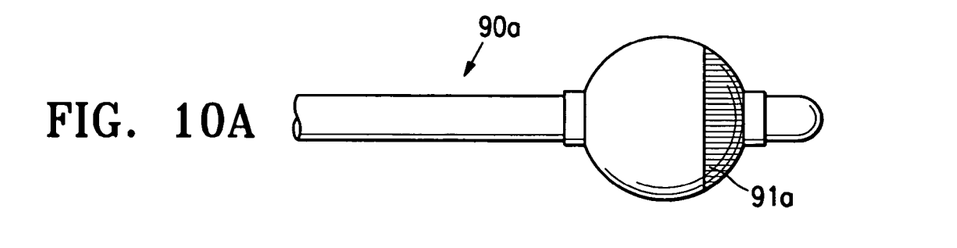
FIGS. 10A and 10B are partial elevational views of distal portions of radiation balloon catheter devices having radiation shield regions on the distal and proximal ends of the balloons. The regions may be hemispherical or cover only a side of the end of the balloon.
Figure 10B:
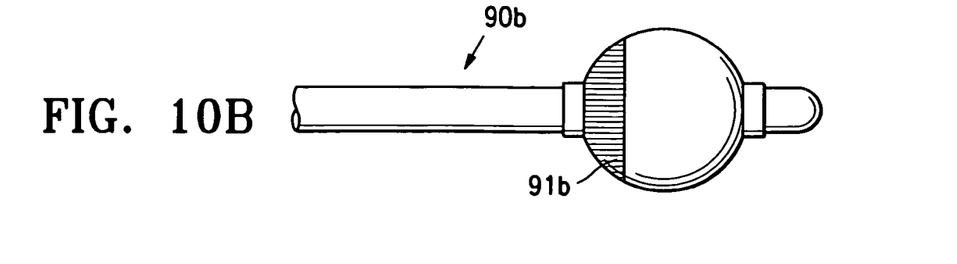

FIGS. 10A and 10B illustrate alternative radiation balloon devices 90A and 90B where the radiation shield regions 91A and 91B are respectively located on the distal and proximal ends of the balloons.

Figure 11A:
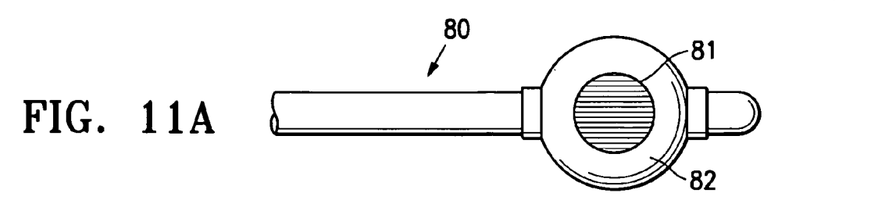
FIGS. 11A and 11B are partial elevational views of distal portions of radiation balloon catheter devices having locator or orientation marks on the balloon.
Figure 11B:
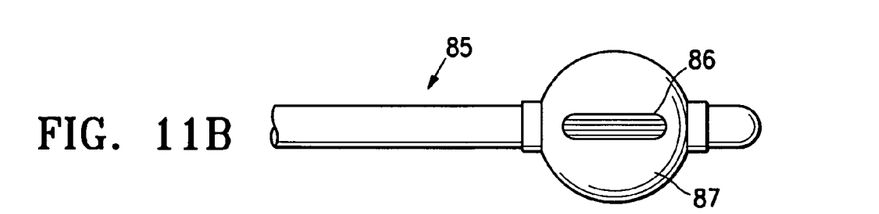

FIGS. 11A and 11B illustrate alternative locator marks on a radiation balloon catheter device such as shown in FIG. 8. In FIG. 11A the locator marks 95 are a series of longitudinally oriented marks both proximal and distal to the radiation absorbing region 96 on the balloon which may be formed of radiopaque materials. In FIG. 11B the locator marks 97 are linear marks extending from the proximal and distal ends of the radiation shielding region 98.

Figures 12, 13:
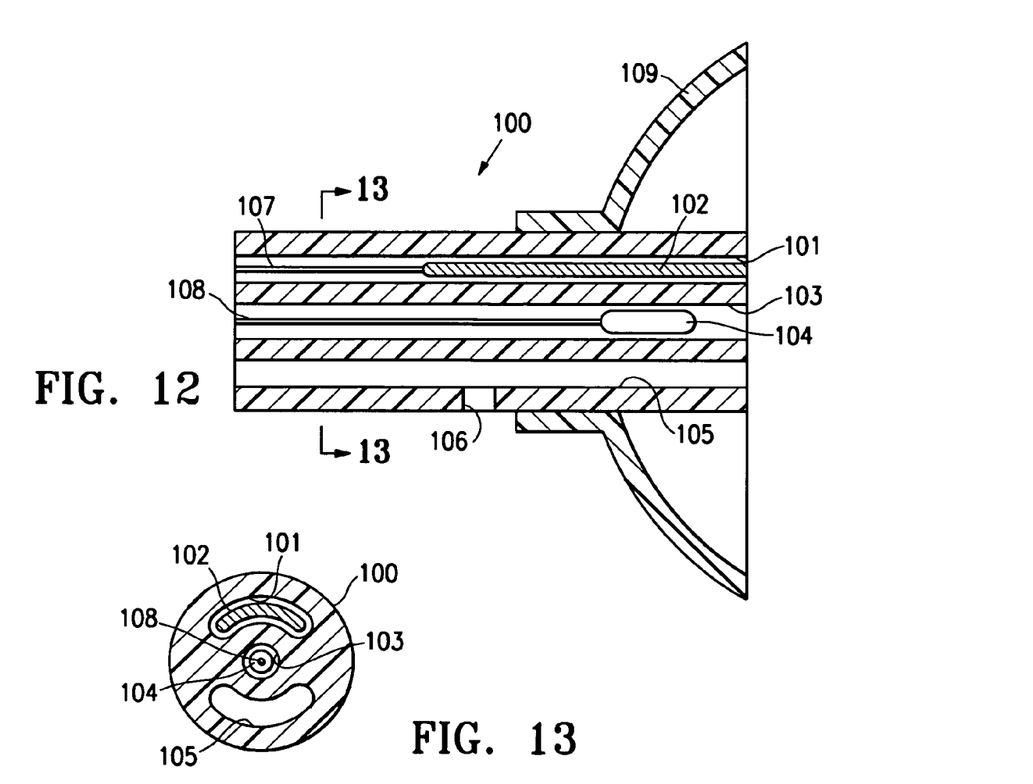
FIG. 12 is a partial longitudinal view, in section, of the elongated shaft of a catheter device having a radiation absorbing shield to control radiation emissions.
FIG. 13 is a transverse cross-sectional view of the device shown in FIG. 12 taken along the lines 13-13.

FIGS. 12 and 13 illustrate a radiation balloon catheter device 100 which has a shield lumen 101 configured to slidably receive radiation shield 102, a radiation source lumen 103 for radiation source 104 and a vacuum lumen 105 for generating a vacuum within the biopsy cavity through port 106. The radiation shield 102 has an elongated shaft 107 for manipulation of the shield for the treatment. While not shown, the proximal end of the shaft 107 is provided with a wing or other extension or indicia to indicate the position of the shield. The radiation source 104 has an elongated shaft 108 to facilitate movement of the radiation source to the desired therapeutic location within the catheter device. The vacuum lumen 105 is utilized for delivery of inflation fluid to the interior of the cavity filling balloon 109.

Figure 14:
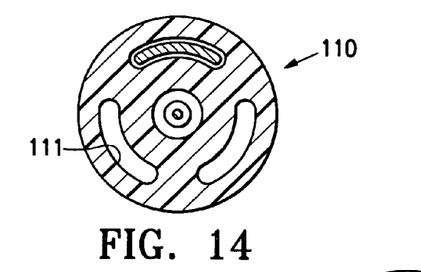
FIG. 14 is a transverse cross-sectional view of a device similar to that shown in FIG. 12 with separate lumens for inflation of the balloon and vacuum delivery.

FIG. 14 is a transverse cross section of an alternative catheter device 110 similar to that shown in FIGS. 12 and 13 but with a separate inflation lumen 111 for delivery of inflation fluid to the interior of the cavity filling balloon (not shown).

Figure 15:
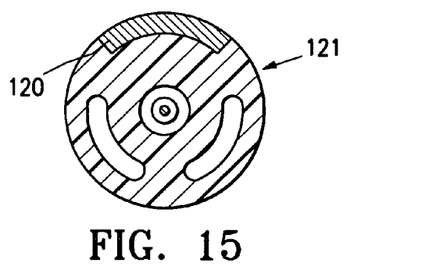
FIG. 15 is a transverse cross-sectional view of a device similar to that shown in FIG. 12 with an alternative structure with a radiation shield fixed within a recess of the inner member within the balloon.
Figure 16:
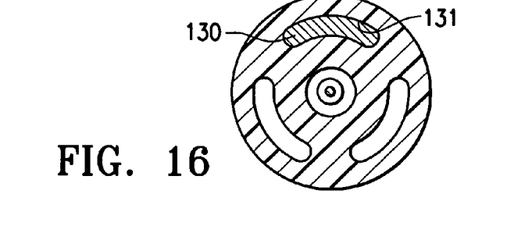
FIG. 16 a transverse cross-sectional view of a device similar to that shown in FIG. 12 with a radiation shield fixed within an inner lumen within the inner member within the balloon.

FIG. 15 illustrates an alternative structure wherein the radiation shield 120 is fixed within a recess in the exterior of inner member 121 FIG. 16 is an alternate structure where the radiation shield 130 is secured within a third inner lumen 131.

Figure 17:
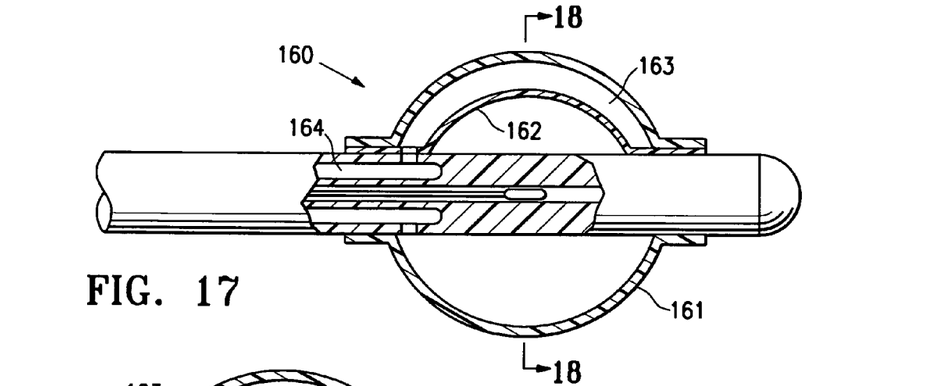
FIG. 17 is an elevational view, partially in section of a device similar to that shown in FIG. 12 with a balloon having a pocket configured to receive radiation absorbing material such as contrast fluid.
Figure 18:
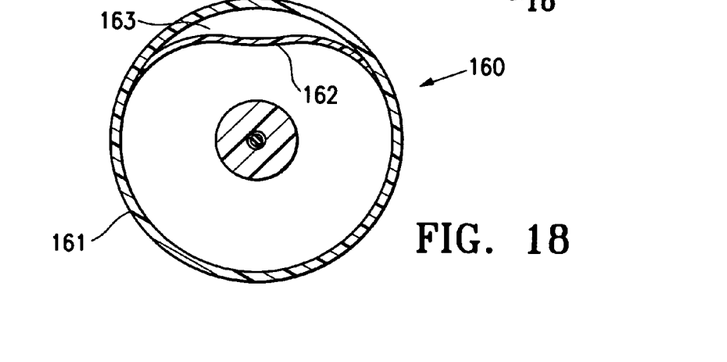
FIG. 18 is a transverse cross-sectional view of the device shown in FIG. 17.

FIGS. 17 and 18 depict an alternative structure for a radiation balloon catheter device 160 embodying features of the invention. In this embodiment the balloon 161 has an inner liner 162 that defines an inner chamber 163 within the balloon that receives contrast fluid from the inner lumen 164. The inner liner 162 as shown is an envelope secured to the interior of the balloon, but it may be formed integrally with the balloon wall. Contrast fluid within the inner chamber 163 shields the tissue adjacent thereto from radiation to avoid tissue damage.

Figure 19A:
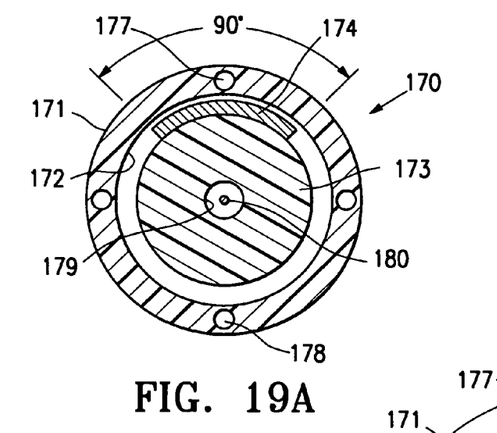
FIGS. 19A-C illustrate another embodiment wherein a radiation shield is provided on an inner catheter which is rotatably disposed within an inner lumen of an outer catheter to reduce radiation on one side of the catheter.
Figure 19B:
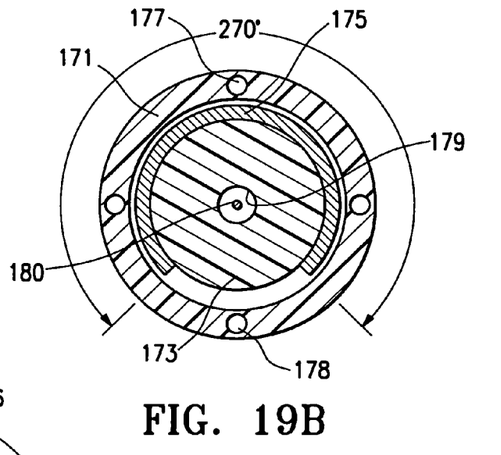
Figure 19C:
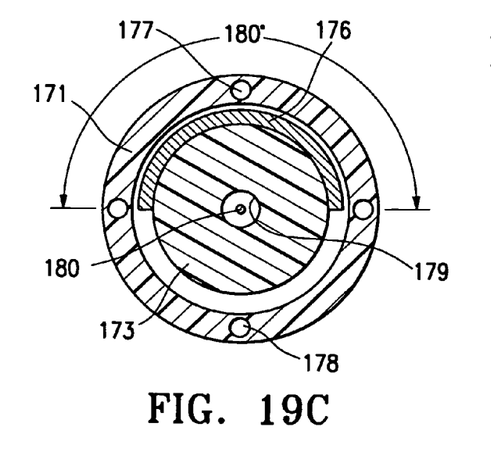

FIG. 19A illustrates a shaft 170 of an alternative device which has an outer catheter 171 with an inner lumen 172, an inner catheter 173 rotatably disposed within inner lumen 172 and a radiation shield 174 on the inner catheter 173. FIGS. 19B and 19C illustrate the same concept except that the radiation shields 175 and 176 cover greater regions of the inner catheter 173 and provide greater angles of radiation attenuation as shown. The outer catheter 171 has an inflatable cavity filling member (not shown) on a distal portion thereof as in the prior examples. The wall of outer catheter 171 has at least one lumen 177 for directing inflation fluid to the interior of the cavity filling member. The outer catheter 121 also has vacuum ports (not shown) proximal and distal to the cavity filling member on the distal portion of the device 170. The wall of the outer catheter 171 also has at least one lumen 178 which is in fluid communication with one or both of the vacuum ports. The inner catheter 173 has a central inner lumen 179 configured to receive a radiation source 180 to provide a radiation dose.

To the extent not otherwise described herein, the device may be formed of conventional materials. The balloon is preferably formed of semi-compliant or non-compliant polymeric materials so that the balloon can be inflated to a predetermined diameter within the body cavity or other site.

While particular forms of the invention have been illustrated and described herein, it will be apparent that various modifications and improvements can be made to the invention. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "elements", "member", "component", "device", "means", "portion", "section", "steps" and words of similar import when used herein shall not be construed as invoking the provisions of 35 U.S.C §112(6) unless the following claims expressly use the terms "means for" or "step for" followed by a particular function without reference to a specific structure of action. All patents and all patent applications referred to above in this application as filed are hereby incorporated by reference in their entirety.

What is claimed is:

1. A device for treating a body cavity or other intracorporeal site within a patient, comprising:
   a.) an elongated shaft having a longitudinal axis, a distal portion with a treatment location and an arcuate shaped lumen which is off set from the longitudinal axis and which extends within the shaft to the treatment location:
   b.) a radiation source configured to be disposed or is disposed in the treatment location; and
   c.) an arcuate shaped radiation shielding component which is slidably disposed within the arcuate shaped lumen and which partially encircles or is configured to partially encircle the treatment location to shield tissue surrounding in part the cavity or other intracorporeal site from radiation emitted from the radiation source and to facilitate irradiation of tissue surrounding the cavity or other intracorporeal site not shielded by the radiation shielding component.

2. The device of claim 1 wherein part of the radiation shielding component is configured to be deployed proximal to the treatment location.

3. The device of claim 1 wherein part of the radiation shielding component is configured to be deployed distal to the treatment location.

4. The device of claim 1 wherein the radiation shield defines in part a window which allows radiation to impinge tissue at the body cavity or other intracorporeal site for treatment.

5. The device of claim 4 wherein the length of the window is about 2 millimeters to about 5 centimeters.

6. The device of claim 5 wherein the radiation shield has an arcuate shielded area with an angular range between about 20° to about 240°.

7. The device of claim 1 wherein the radiation shielding component slidably disposed within the elongate shaft has a distal radiation shield configured to be deployed distal to the treatment location and a proximal radiation shield configured to be deployed proximal to the treatment location.

8. The device of claim 7 wherein spacing between the proximal and distal radiation shields is adjustable.

9. The device of claim 8 wherein spacing between the proximal and distal radiation shields is partially shielded by the central radiation shield which partially encircles the treatment location and extends between the proximal and distal radiation shields.

10. The device of claim 1 wherein the elongated shaft is partitioned to provide a plurality of lumens divided by spacing elements that are configured to receive shielding shields.

11. The device of claim 1 including an elongated shaft which has an inner lumen leading to the treatment location configured to deliver the radiation source to the treatment location.

12. The device of claim 11 wherein the radiation source is a solid material.

13. The device of claim 12 wherein the radiation source is a brachytherapy seed.

14. The device of claim 11 wherein the radiation source is selected from the group consisting of a liquid containing a radioactive iodine isotope, a slurry containing a solid radioactive isotope, a gel containing a solid radioactive isotope, or a microminiature x-ray tube.

15. The device of claim 1 including a cavity filling member which at least in part fills the body cavity or other intracorporeal site and which surrounds at least in part the treatment location.

16. The device of claim 15 wherein the cavity filling member is expandable.

17. The device of claim 16 wherein the cavity filling member is inflatable.

18. The device of claim 17 wherein the cavity filling member has an interior configured to receive inflation fluid.

19. The device of claim 18 wherein the cavity filling member is a balloon.

20. The device of claim 19 including an inflation lumen which is in fluid communication with an interior of the balloon.

21. The device of claim 15 wherein the radiation shielding component is part of the cavity filling member.

22. The device of claim 21 wherein the radiation shielding portion of the cavity filling member has an oval shape.

23. The device of claim 22 wherein the oval shaped radiation shielding portion of the cavity filling member is longitudinally oriented.

24. The device of claim 21 wherein the radiation shielding portion of the cavity filling member has a circular shape.

25. The device of claim 21 wherein the radiation shielding portion of the cavity filling member has the shape of a spherical segment and is located at an end of the cavity filling member.

26. The device of claim 15 wherein the cavity filling member is spherical shaped.

27. The device of claim 15 wherein the cavity filling member is oval shaped.

28. The device of claim 1 wherein the radiation shielding component is formed at least in part of radiation absorbing material.

29. The device of claim 28 wherein the radiation absorbing material is selected from a group consisting of tantalum, bismuth subcarbonate, barium sulfate, platinum, gold, and tungsten.

30. The device of claim 1 wherein a portion of the radiation shielding component contains a lesser amount of the radiation absorbing material than other portions of the radiation shielding component.

31. The device of claim 1 including an elongated shaft which has a vacuum lumen configured to be in fluid communication with a vacuum source and one or more vacuum ports in the exterior of the elongated shaft to provide a vacuum within the body cavity or other intracorporeal site.

32. A system for treating a body cavity or other intracorporeal site within a patient, comprising:
   a.) an elongate shaft having a proximal end, a distal end, and a treatment location in a distal portion of the elongate shaft, first and second lumens extending within the shaft to the treatment location;
   b.) a source for a treatment agent configured to be disposed in the treatment location; and
   c.) a cavity filling member on the elongated shaft surrounding the treatment location having an interior which is in fluid communication with the first lumen;
   d.) a source for inflation fluid which is in fluid communication with the first lumen;
   a.) an bladder within the cavity filling member defining at least in part an separate chamber within the interior of the cavity filling member which is in fluid communication with and receives contrast material from the second lumen and which is at least in part spaced away from the elongated shaft.

33. The system of claim 32 wherein the treatment agent is a radiation source.

34. The system of claim 33 wherein the radiation source is a brachytherapy seed.

35. The system of claim 33 wherein the radiation source is selected from the group consisting of a liquid containing a radioactive iodine isotope, a slurry containing solid radioactive isotope, a gel containing a solid radioactive isotope, or a microminiature x-ray tube.

36. The system of claim 32 wherein the device has an third lumen configured to deliver the treatment agent to the treatment location at the distal portion of the shaft.

37. The system of claim 33 wherein the cavity filling member is configured to at least partially fill the body cavity.

* * * * *